US009717593B2

(12) United States Patent
Alkhatib et al.

(10) Patent No.: US 9,717,593 B2
(45) Date of Patent: Aug. 1, 2017

(54) LEAFLET SUTURING TO COMMISSURE POINTS FOR PROSTHETIC HEART VALVE

(75) Inventors: Yousef F. Alkhatib, Edina, MN (US); Peter Nicholas Braldo, Wyoming, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 148 days.

(21) Appl. No.: 13/216,124

(22) Filed: Aug. 23, 2011

(65) Prior Publication Data
US 2012/0197391 A1 Aug. 2, 2012

Related U.S. Application Data

(60) Provisional application No. 61/438,451, filed on Feb. 1, 2011.

(51) Int. Cl.
*A61F 2/24* (2006.01)
*A61F 2/95* (2013.01)

(52) U.S. Cl.
CPC .......... *A61F 2/2418* (2013.01); *A61F 2/2412* (2013.01); *A61F 2/2436* (2013.01); *A61F 2002/9517* (2013.01); *A61F 2002/9534* (2013.01); *A61F 2220/0075* (2013.01); *A61F 2230/0013* (2013.01); *A61F 2250/0039* (2013.01)

(58) Field of Classification Search
CPC .............................. A61F 2/2412; A61F 2/2418
USPC ............ 623/1.24, 1.26, 2.1, 2.11, 2.12, 2.13, 623/2.14, 2.15, 2.16, 2.17, 2.18, 2.19, 623/2.38, 2.39, 2.4, 2.41, 900, 910
See application file for complete search history.

(56) References Cited

U.S. PATENT DOCUMENTS

| 6,682,559 | B2 * | 1/2004 | Myers et al. ................. 623/2.13 |
| 6,736,845 | B2 | 5/2004 | Marquez et al. |
| 6,893,460 | B2 | 5/2005 | Spenser et al. |
| 7,018,406 | B2 | 3/2006 | Seguin et al. |
| 7,329,278 | B2 | 2/2008 | Seguin et al. |
| 8,313,525 | B2 * | 11/2012 | Tuval .................... A61F 2/2418 623/2.11 |
| 8,568,475 | B2 * | 10/2013 | Nguyen et al. ............. 623/2.12 |
| 8,652,202 | B2 * | 2/2014 | Alon ..................... A61F 2/2418 623/2.11 |

(Continued)

FOREIGN PATENT DOCUMENTS

WO 2009/042196 A2 4/2009

OTHER PUBLICATIONS

International Search Report Application No. PCT/US2011/048963, dated Dec. 15, 2011.

(Continued)

*Primary Examiner* — David Isabella
*Assistant Examiner* — Suba Ganesan
(74) *Attorney, Agent, or Firm* — Lerner, David, Littenberg, Krumholz & Mentlik, LLP (57) ABSTRACT

A collapsible prosthetic heart valve includes a collapsible and expandable stent and a collapsible and expandable valve assembly. The stent has a proximal end and a distal end. A plurality of commissure points is disposed on the stent. The valve assembly is disposed within the stent and includes a plurality of leaflets. Each leaflet has a free edge. An end portion of the free edge of each leaflet is folded and sutured to a corresponding one of the plurality of the commissure points.

9 Claims, 10 Drawing Sheets (56) References Cited

U.S. PATENT DOCUMENTS

| | | | |
|---|---|---|---|
| 2004/0186563 A1* | 9/2004 | Lobbi | 623/2.18 |
| 2005/0004583 A1 | 1/2005 | Oz et al. | |
| 2006/0025857 A1* | 2/2006 | Bergheim | A61F 2/2409 623/2.18 |
| 2006/0259136 A1* | 11/2006 | Nguyen | A61F 2/2412 623/2.18 |
| 2006/0259137 A1* | 11/2006 | Artof | A61F 2/2418 623/2.18 |
| 2008/0004688 A1* | 1/2008 | Spenser et al. | 623/1.13 |
| 2008/0071369 A1 | 3/2008 | Tuval et al. | |
| 2008/0147179 A1 | 6/2008 | Cai et al. | |
| 2008/0228264 A1 | 9/2008 | Li et al. | |
| 2008/0269878 A1 | 10/2008 | Iobbi | |
| 2009/0157175 A1* | 6/2009 | Benichou | A61F 2/2412 623/2.18 |
| 2010/0049313 A1 | 2/2010 | Alon et al. | |
| 2010/0204781 A1 | 8/2010 | Alkhatib | |
| 2010/0249911 A1 | 9/2010 | Alkhatib | |

OTHER PUBLICATIONS

International Search Report Application No. PCT/US2011/048989, dated Dec. 15, 2011.
International Search Report Application No. PCT/US2011/048967, dated Dec. 15, 2011.

\* cited by examiner

FIG. 5C ated patent application No. 61/438,451, filed Feb. 1, 2011, the disclosure of which is hereby incorporated herein by reference.

LEAFLET SUTURING TO COMMISSURE POINTS FOR PROSTHETIC HEART VALVE

CROSS-REFERENCE TO RELATED APPLICATIONS

This application claims the benefit of the filing date of U.S. Provisional Patent Application No. 61/438,451, filed Feb. 1, 2011, the disclosure of which is hereby incorporated herein by reference.

BACKGROUND OF THE INVENTION

The present invention relates to heart valve replacement and, in particular, to collapsible prosthetic heart valves. More particularly, the present invention relates to collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve assembly or structure mounted on a stent. There are many types of stents that may be used. However, two types of stents on which the valve structures are ordinarily mounted include: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implantation site in the patient (e.g., at or near the annulus of the patient's heart valve that is to be replaced by the prosthetic valve), the prosthetic valve can be deployed or released from the delivery apparatus and expanded to the full operating size. For balloon-expandable stents, this generally involves releasing the entire valve, assuring its proper location, and then expanding a balloon positioned within the stent. For self-expanding stents, on the other hand, the stent automatically expands as the sheath covering the valve is withdrawn.

The leaflets in a collapsible prosthetic heart valve, over their useful life, must open and close millions of times. This repeated movement can cause various stresses on the leaflets and, in particular, where they are secured to the rest of the valve. Improper or inadequate attachment can lead to tearing of pulling away from the stent and failure of the valve. And valve failure, in the circulatory system, can have significant consequences for the patient. Accordingly, there remains a need for improved methods of producing heart valves and securing valve leaflets in collapsible prosthetic heart valves.

SUMMARY OF THE INVENTION

The present disclosure relates to prosthetic heart valves. In one embodiment, the prosthetic heart valve includes a stent and a valve assembly. The stent has a collapsed condition and an expanded condition and includes a plurality of commissure points disposed thereon. The valve assembly is secured to the stent and includes a plurality of leaflets. Each leaflet includes a free edge. An end portion of the free edge of the leaflet is folded and sutured to a corresponding one of the plurality of the commissure points.

In an embodiment of the present invention, the end portions of the free edges of first and second adjacent leaflets are sutured to one another. In another embodiment, the prosthetic heart valve further includes a reinforcement layer disposed between the folded end portions of the free edge of the leaflet.

In certain embodiments of the present invention, the folded end portion of the free edge of the leaflet is generally parallel to the immediately adjacent portions of the leaflet and/or generally perpendicular to the commissure point. In other embodiments, the folded end portion of the free edge of the leaflet is generally perpendicular to the immediately adjacent portions of the leaflet and/or generally parallel to the commissure point.

The free end of the folded end portion of the free edge of the leaflet may extend beyond the suture toward the immediately adjacent portion of the leaflet. In yet another embodiment, the end portion of the free edge of the leaflet may be rolled into a generally spiral configuration. In still another embodiment, the folded end portion of the free edge of the leaflet may include two or more folds.

The end portion of the free edge of the leaflet may wrap at least partially around the commissure point. A web overlying the end portion of the free edge of the leaflet may substantially wrap around the commissure point and may be sutured to be end portion and the commissure point.

Moreover, the leaflet may include "tabs" or ends which are attached to the commissure points or a portion of the attached edge may be sutured thereto.

According to yet another embodiment of the present invention, a prosthetic heart valve includes a stent and a valve assembly disposed within the stent. Each of the stent and the valve assembly has a collapsed condition and an expanded condition. The stent has a proximal end and a distal end. A plurality of commissure points is disposed on the stent. The valve assembly includes a plurality of leaflets, each of which has a free edge. An end portion of the free edge of the leaflet is folded and sutured to a corresponding one of the commissure points. The end portion is folded in a configuration selected from the group consisting of a U-shaped pleat, an S-shaped pleat, a generally spiral roll and a U-shaped pleat enveloped by an external web.

BRIEF DESCRIPTION OF THE DRAWINGS

Various embodiments of the present inventions are disclosed herein with reference to the drawings, wherein.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient.

Figure 1:
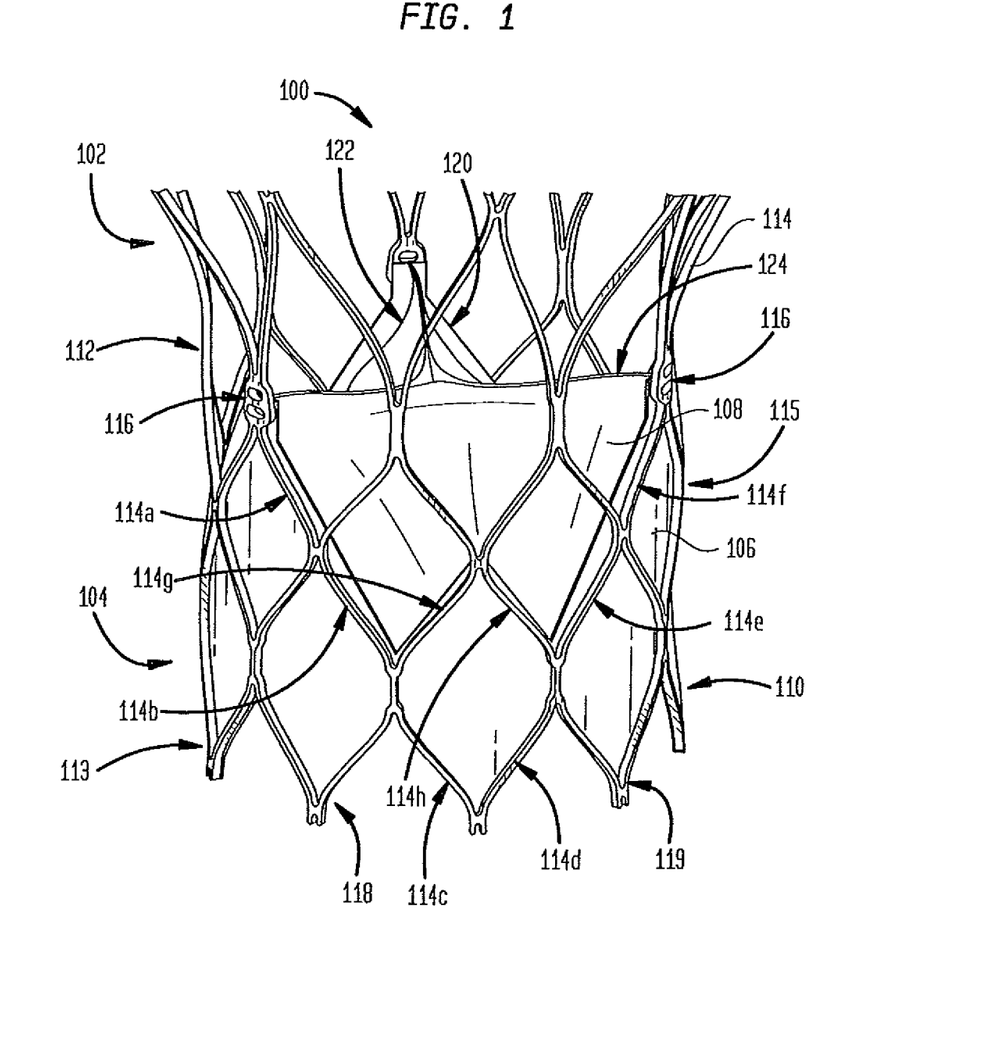
FIG. 1 is a partial side elevational view of a collapsible prosthetic heart valve according to an embodiment of the present invention.

As seen in FIG. 1, a collapsible prosthetic heart valve 100 typically includes a stent or frame 102 supporting a valve assembly 104. Examples of collapsible prosthetic heart valves are described in International Patent Application Publication No. WO/2009/042196; U.S. Pat. Nos. 7,018, 406; 7,329,278, United States Patent Application Publication Nos. 2005/0113910 and 2009/0030511, the disclosures of all of which are hereby incorporated herein by reference.

The prosthetic heart valve 100 is designed to replace the function of a native aortic valve of a patient. As discussed in detail below, the prosthetic heart valve has an expanded condition and a collapsed condition. Although the invention is described herein as applied to a prosthetic heart valve for replacing a native aortic valve, the invention is not so limited, and may be applied to prosthetic valves for replacing other types of cardiac valves.

The prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. The stent 102 may have an annulus section 110 and an aortic section (not shown). Each of the annulus section 110 and the aortic section of the stent 102 includes a plurality of cells 112 connected to one another around the stent. The annulus section 110 and the aortic section of the stent 102 may include one or more annular rows of cells 112 connected to one another. For instance, the annulus section 110 may have two annular rows of cells 112. When the prosthetic heart valve 100 is in the expanded condition, each cell 112 may be substantially diamond shaped. Regardless of its shape, each cell 112 is formed by a plurality of struts 114. For example, a cell 112 may be formed by four struts 114.

The stent 102 may include commissure points 116 connecting at least two cells 112 in the longitudinal direction of the stent 102. The commissure points 116 may include eyelets for facilitating the suturing of a valve assembly 104 to the stent 102.

The prosthetic heart valve 100 also includes a valve assembly 104 attached inside the annulus section 110 of the stent 102. United States Patent Application Publication Nos. 2008/0228264, filed Mar. 12, 2007; 2008/0147179, filed Dec. 19, 2007; 2005/0113910, filed Jul. 10, 2004; and 2009/0030511, filed Jan. 29, 2009, the entire disclosures of all of which are hereby incorporated herein by reference, describe suitable valve assemblies. The valve assembly 104 may be wholly or partly formed of any suitable biological material or polymer materials in the forms of sheets, non-woven and woven fabrics and the like. Examples of biological materials suitable for the valve assembly 104 include, but are not limited to, porcine or bovine pericardial tissue. Examples of polymers suitable for the valve assembly 104 include, but are not limited to, polyurethane and polyester.

The valve assembly 104 may include a cuff 106 disposed on the lumenal surface of annulus section 110, on the ablumenal surface of annulus section 110, or on both surfaces, and the cuff may cover all or part of either or both of the lumenal and ablumenal surfaces of the annulus section. FIG. 1 shows cuff 106 disposed on the lumenal surface of annulus section 110 so as to cover part of the annulus section while leaving another part thereof uncovered. The valve assembly 104 may further include a plurality of leaflets 108 which collectively function as a one-way valve. A first edge 122 of each leaflet 108 may be attached to the stent 102 by any suitable attachment means, such as suturing, stapling, adhesives or the like. A second or free edge 124 of each leaflet 108 may coapt with the corresponding free edges of the other leaflets, thereby enabling the leaflets to function collectively as a one-way valve.

Irrespective of the attachment means employed, the leaflets 108 may be attached to the stent 102 along at least some struts 114 of the stent 102 to enhance the structural integrity of the valve assembly 104. As a consequence of this attachment, the struts 114 help support the leaflets 108 of the valve assembly 104 and may therefore reduce the strain in the leaflets.

As shown in FIG. 1, at least one leaflet 108 may be attached to the stent 102 so that its first edge 122 is disposed substantially along specific struts 114a, 114b, 114c, 114d, 114e and 114f located in the annulus section 110 of the stent. That is, the edge 122 is positioned in substantial alignment with struts 114a, 114b, 114c, 114d, 114e, and 114f. Also as shown, the edge 122 can be roughly parallel to the edge of the cuff 106. However, of course, the cuff 106 need not be cut to follow the slope or pattern of the struts. Struts 114a, 114b, and 114c may be connected to one another in substantially end-to-end fashion diagonally along three cells 112, beginning with an end of the strut 114a connected to a commissure point 116 and ending with an end of strut 114c connected to an end of strut 114d. Struts 114c and 114d are part of the same cell 112 and may collectively define a substantially right angle between them. Struts 114d, 114e, and 114f may be connected to one another in substantially end-to-end fashion diagonally along three cells 112, beginning with an end of the strut 114f connected to a commissure point 116 and ending with the connection between an end of strut 114c and an end of strut 114d.

As discussed above, the leaflets 108 may be attached directly to and supported by the struts 114a, 114b, 114c, 114d, 114e, and 114f, such as by suturing. In such event, the cuff 106 may perform little or no supportive function for the leaflets 108, and the thickness of the cuff 106 may, therefore, be reduced. Reducing the thickness of the cuff 106 results in a decrease in the volume of the valve assembly 104 in the collapsed condition. This decreased volume is desirable as it enables the prosthetic heart valve 100 to be implanted in a patient using a delivery device that is smaller than conventional delivery devices. In addition, since the material forming the stent 114 is stronger than the material forming the cuff 106, the stent may perform the supportive function for the leaflets 108 better than the cuff.

The volume of the valve assembly 104 may be further reduced by having the cuff 106 cover only a portion of the surface of annulus section 110. With continued reference to FIG. 3, the first or proximal end 118 of the cuff 106 may substantially follow the contour of the first or proximal end 119 of the stent 102. As such, the proximal end of the cuff 106 may have a generally sinusoidal or zigzag shape. This eliminates any free edge of the cuff 106, which otherwise might extend directly between the cusps of the cells 112 at the proximal end 119 of the stent 102, and enables the entire length of the proximal end 118 of the cuff 106 to be secured to the stent 102. The second or distal end 120 of the cuff 106, on the other hand, may be disposed substantially along at least some struts 114, but not necessarily the struts in a single annular row of cells 112.

More particularly, the distal end 120 of the cuff 106 may follow the stent struts 114 up to the commissure points 116, such that the cuff 106 covers all of the cells 112 in the bottom annular row 113 of cells 112 and in a second annular row 115 of cells located between the commissure points and the proximal end 119 of the stent 102, but covers a lesser area of cells in the annular regions between the commissure points. In other words, the distal end 120 of the cuff 106 may be disposed substantially along struts 114a, 114b, 114e, 114f, 114g and 114h, as shown in FIG. 1. Strut 114g may be connected at one end to strut 114h, and at the other end to the intersection of struts 114b and 114c. Strut 114h may be connected at one end to strut 114g, and at the other end to the intersection of struts 114d and 114e. Struts 114c, 114d, 114g, and 114h collectively form a single cell 112.

As a result of the foregoing configuration, all of the cells 112 in the bottom annular row 113 of cells 112 may be entirely covered by the cuff 106. The cuff 106 may also entirely cover those cells 112 in the second annular row 115 that are located directly below the commissure points 116. All of the other cells 112 in the stent 102 may be open or not covered by the cuff 106. Hence, there may be no cells 112 which are only partially covered by the cuff 106.

Since the edges of the valve leaflets 108 extend up to the second annular row 115 of cells 112 only in the regions of the commissure points 116, there is little to no likelihood of leakage in the area of the cells between the commissure points in the second annular row of cells, and therefore no need for the cuff 106 to cover this area. This reduction in the area of the cuff 106, both at the proximal end 118 and at the distal end 120 thereof, reduces the amount of material in the valve assembly 104, thereby enabling the prosthetic valve 100 to achieve a smaller cross-section in the collapsed condition.

Figure 2:
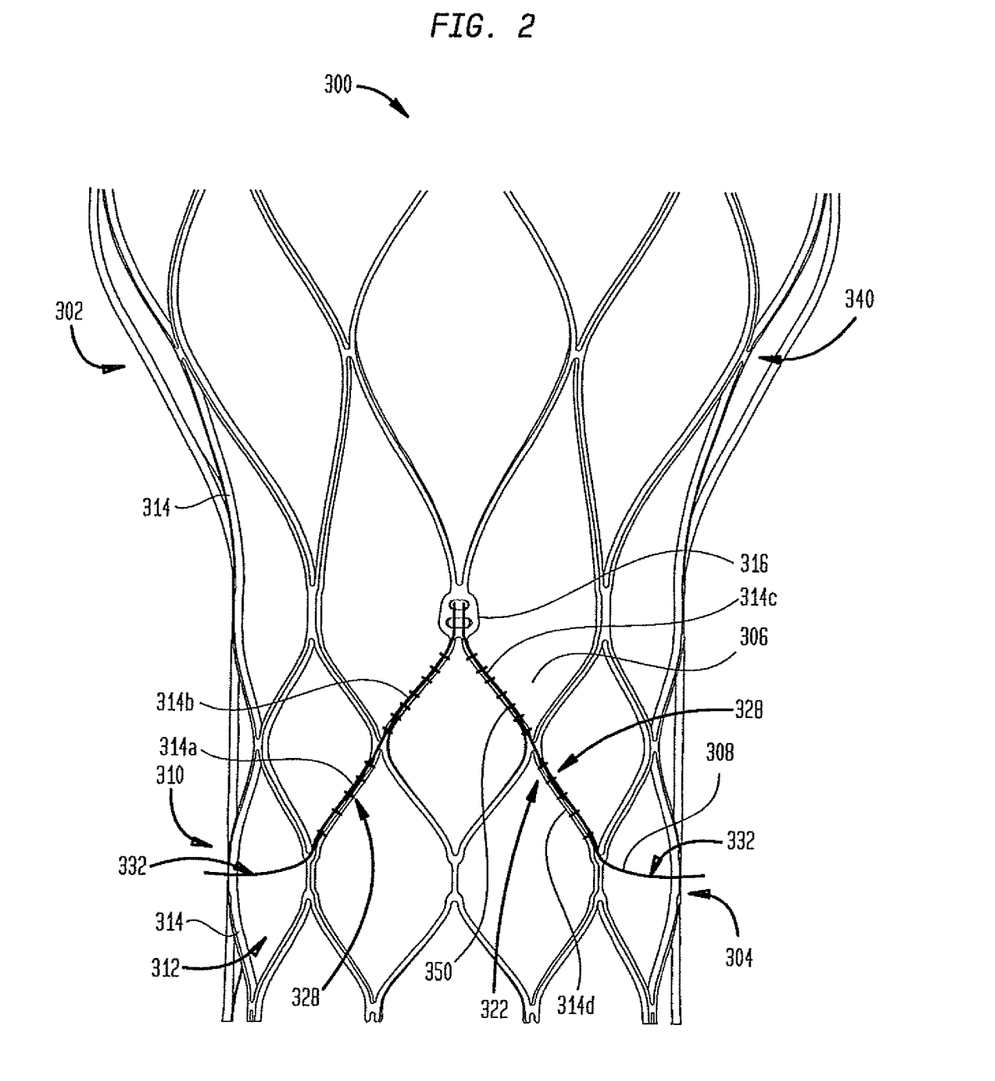
FIG. 2 is a developed view of a portion of a collapsible prosthetic heart valve according to a further embodiment of the present invention in which an edge of the leaflets is disposed substantially along several stent struts.

With reference to FIG. 2, a prosthetic heart valve 300 according to another embodiment of the present invention includes a stent or frame 302, which may be similar to stent 102. The stent 302 may include an aortic section 340 and an annulus section 310. Each of the aortic section 340 and the annulus section 310 may include a plurality of cells 312 connected to one another in one or more annular rows. The cells 312 of the aortic section 340 may be larger than the cells of the annulus section 310. Each cell 312 is formed by a plurality of struts 314. For example, each cell 312 may be formed by four struts 314 and may be substantially diamond-shaped when the stent 302 is in an expanded condition. The stent 302 may further include one or more commissure points 316 for facilitating suturing of a valve assembly 304 to the stent. Each commissure point 316 may interconnect two cells 312 in the same annular row and two cells in different annular rows.

The valve assembly 304 may be attached inside the stent 302, and may include a cuff 306 and a plurality of leaflets 308 which collectively function as a one-way valve. The cuff 306 may be located on the inside surface of the stent 302, on the outside surface of the stent, or on both the inside surface and the outside surface. Each leaflet 308 includes an edge 322 attached to the stent 302 and a second free edge 324. An upper portion 328 of the edge 322 may be attached to the stent 302 so as to be disposed substantially along the path of certain struts 314 that lead to the commissure points 316. For example, an upper portion 328 of the edge 322 of at least one leaflet 308 may be attached to, and disposed substantially along, struts 314a and 314b, and an upper portion 328 of the edge 322 of an adjacent leaflet 308 may be attached to, and disposed substantially along, struts 314c and 314d. As such, struts 314a, 314b, 314c, and 314d help support these adjacent leaflets 308. The upper portions 328 of the edges 322 of adjacent leaflets 308 may be attached to the commissure point 316 and struts 314a, 314b, 314c, and 314d using sutures 350. Struts 314b and 314c may each have one end attached to a commissure point 316 and each may be part of the same cell 312.

Alternatively, struts 314b and 314c may be attached directly to one another. Struts 314a and 314b may be connected in an end-to-end fashion, and may be part of different cells 312 that are adjacent to one another. Similarly, struts 314c and 314d may be connected in an end-to-end fashion, and may be part of different cells 312 that are adjacent to one another.

Figure 3:
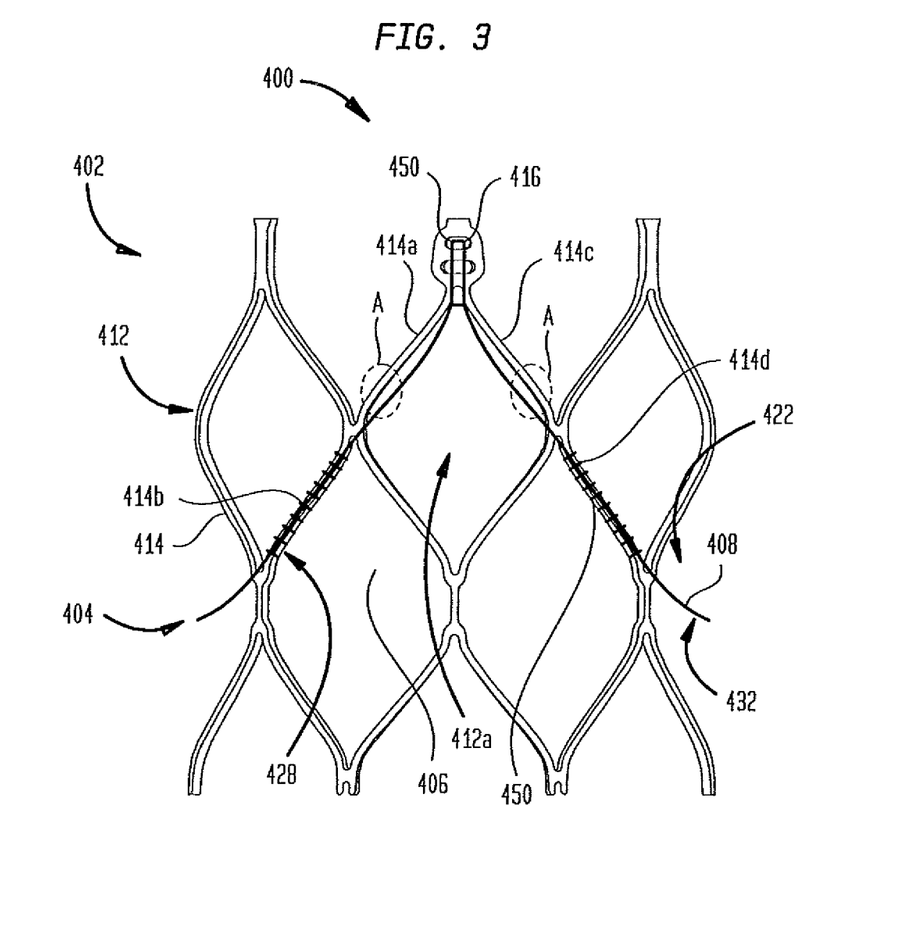
FIG. 3 is a developed view of a portion of a collapsible prosthetic heart valve according to yet another embodiment of the present invention in which some portions of the leaflets of the valve assembly are attached to the stent and disposed substantially along certain stent struts.

With reference to FIG. 3, a collapsible prosthetic heart valve 400 according to an embodiment of the present invention includes a stent 402, which may be similar to stent 102. The stent 402 has collapsed and expanded conditions and includes a plurality of cells 412 connected to one another in annular rows around the stent 402. Each cell 412 is formed by a plurality of struts 414 and may be substantially diamond shaped when the stent 402 is in the expanded condition. For example, one cell 412 may be formed by four interconnected struts 414.

The stent 402 may further include one or more commissure points 416 that interconnect two adjacent cells 412 located in one annular row and two other cells 412 located in the next adjacent rows above and below the one row. The commissure points 416 may facilitate the suturing of a valve assembly 404 to the stent 402.

The valve assembly 404 may include a cuff 406 attached to the interior and/or exterior of the stent 402. In addition to the cuff 406, the valve assembly 404 includes a plurality of leaflets 408 attached to the stent 402 and collectively defining a one-way valve. Each leaflet 408 includes a first edge 422 attached to the stent 402 and a second free edge 424. At least one leaflet 408 may be attached to the stent 402 so that the upper portions 428 of its edge 422 are substantially disposed along the path of certain struts 414.

As shown in FIG. 3, one upper portion 428 of the edge 422 of one leaflet 408 may be connected to a commissure point 416 and may be disposed along and connected to a strut 414b spaced from the commissure point. A section A of the upper portion 428 of the edge 422 may follow a substantially direct path between the commissure point 416 and an end of stent strut 414b. Similarly, one upper portion 428 of the edge 422 of another leaflet 408 may be connected to the commissure point 416 and may be disposed along and connected to a strut 414d spaced from the commissure point. A section A of the upper portion 428 of the edge 422 of this second leaflet 408 may follow a substantially direct path between the commissure point 416 and an end of stent strut 414d. The edges 422 of the leaflets 408 may be connected to the commissure point 416 and to the struts 414b and 414d using sutures.

In operation, any of the embodiments of the prosthetic heart valve described above may be used to replace a native heart valve, such as the aortic valve. The prosthetic heart valve may be delivered to the desired site (e.g., near a native valve annulus) using any suitable delivery device known in the art. During delivery, the prosthetic heart valve is disposed inside the delivery device in the collapsed condition. The delivery device may be introduced into a patient using the transfemoral, transapical or transseptal approach. Once the delivery device has reached the target site, the user may deploy any of the prosthetic heart valves described above. Upon deployment, the prosthetic heart valve expands into secure engagement within the native valve annulus. When the prosthetic heart valve is properly positioned inside the heart, it works as a one-way valve, allowing blood to flow in one direction and preventing blood from flowing in the opposite direction.

In each of the prosthetic heart valve embodiments described above, the valve assembly preferably is spaced from the distal or aortic end of the stent by a distance that enables deployment of the heart valve by an amount sufficient for the valve leaflets of the prosthetic valve to operate as intended, while the distal end of the stent remains captured by the delivery device. More particularly, the annulus end of the prosthetic heart valve may be deployed first while the aortic end of the prosthetic heart valve remains at least partially covered by the distal sheath of the delivery device. The annulus portion of the prosthetic heart valve may be deployed so that the entirety of the valve leaflets, up to and including the commissures, is deployed and fully operational. By deploying the prosthetic heart valve in this manner, the user can determine whether the valve leaflets are properly positioned relative to the native valve annulus, and whether the valve is functioning properly.

If the user determines that the positioning and operation of the valve are acceptable, the remainder of the valve may be deployed. However, if it is determined that the leaflet position is improper or that the valve is not functioning properly, the user may resheath the valve and either reposition it for redeployment, or remove it entirely from the patient. This can be particularly important in very high risk patients who would typically be recipients of these types of valves, because of the nature of their condition and the impact that may have on the shape and/or condition of the native valve and valve annulus. Of course, the prosthetic heart valve of the present invention can be delivered by deploying the aortic or distal end first as well.

Anatomical irregularities at the implantation site can create issues with respect to the proper functioning and wear of the prosthetic heart valve. Another aspect of the invention is the achievement of a better functioning valve in the various shapes, such as elliptical, round, irregular, etc., that the valve may assume upon implantation and use. This may depend, in some instances, not only on leaflet positioning, commissure positioning, and valve geometry, as previously described, but also can relate to the manner in which the leaflets are attached to the valve assembly, the stent, and in particular, the commissure attachment points. As the stent is deformed by implantation and use, if leaflet positioning and geometry are not correct, undesirable load forces at the leaflet edges, particularly at the commissure attachment points, can be created. This can lead to tearing of the leaflets and/or cuff and eventually valve failure.

Some arrangements that are intended to minimize valve failure and promote better valve function are illustrated in FIGS. 4A-4I. FIGS. 4A-4I show various arrangements for attaching the leaflets to the commissure points 116 in order to promote better and longer valve function. Which particular arrangement is used may depend, inter alfa, on the type of valve material used, the thickness of the stent, the dimensions of the commissure points, the type, thickness and placement of the cuff, if any, the overall shape of the valve and valve assembly, and the like. Note that in the various illustrations which represent the end views, as seen from the distal end of the stent along the longitudinal axis of the stent toward the proximal end of the stent, of a commissure point and the attachment of the leaflets thereto (in which the dashed lines represent suture lines), the cuff is not illustrated for purposes of clarity.

Figure 4A:
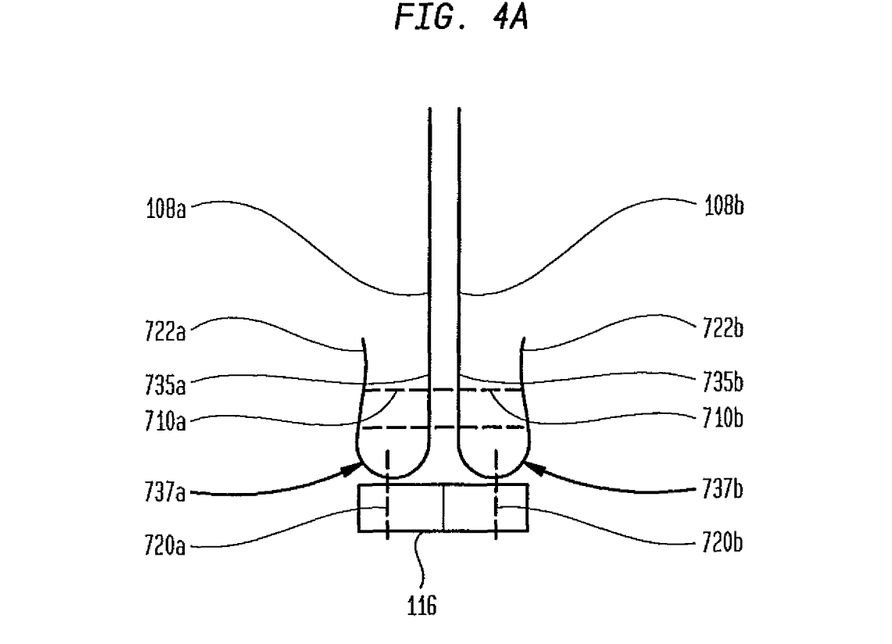
FIGS. 4A-4I are highly schematic end views showing various embodiments of leaflet suturing to a commissure point of the stent according to aspects of the present invention.

Referring to FIG. 4A, portions of two adjacent leaflets 108a and 108b are illustrated. Note that the leaflets 108a and 108b are illustrated as generally parallel to each other only for the sake of simplicity. In actuality, the adjacent leaflets 108a, 108b will generally diverge from one another as they extend away from the commissure point 116. In the illustrated embodiment, an end portion 722a of leaflet 108a is folded in a generally "U-shaped" pleat 737a. Likewise, an end portion 722b of leaflet 108b is folded in a generally "U-shaped" pleat 737b. The folded end portions 722a, 722b may be generally parallel to the immediate adjacent portions 735a, 735b, respectively, of the leaflets 108a, 108b and generally perpendicular to the commissure point 116. The folded end portions 722a, 722b may be sutured to one another by one or more sutures 710 (a pair of sutures illustrated). In addition, end portion 722a may be sutured to commissure point 116 via one or more sutures 720a and end portion 722b may be sutured to commissure point 116 via one or more sutures 720b (a single suture illustrated). Since the sutures 710a, 710b pass through the U-shaped pleats 737a, 737b, respectively, the stresses induced in the leaflet 108a, 108b due to the sutures at the sites of the sutures may be more widely distributed, thereby minimizing the likelihood of a tear in the leaflets due to suturing.

Figure 4B:
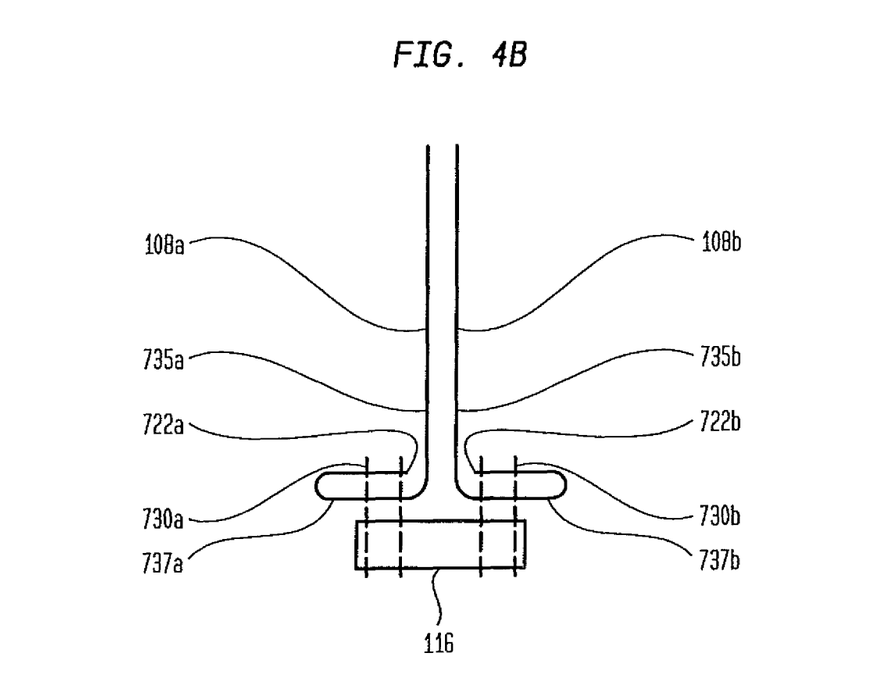

FIG. 4B illustrates the suturing of the leaflets to the commissure point 116 according to another embodiment of the invention. Each of the end portions 722a, 722b of the respective leaflets 108a, 108b is folded in a generally "U-shaped" pleat 737a, 737b, respectively, as in the embodiment of FIG. 4A, and the U-shaped pleats 737a, 737b are then bent outwardly so as to lie substantially perpendicular to the immediate adjacent portions 735a, 735b of the leaflets 108a, 108b and generally parallel to the commissure point 116. The U-shaped pleat 737a may be sutured to the commissure point 116 via one or more sutures 730a. Similarly, the U-shaped pleat 737b may be sutured to the commissure point 116 via one or more sutures 730b. In variants hereof, less than or more than two sutures may be employed to suture each folded end portion 722a, 722b to the commissure point 116. Since sutures 730a, 730b pass through the U-shaped pleats 737a, 737b, respectively, the stresses induced in the leaflets 108a, 108b at the sites of the sutures may be more widely distributed, thereby minimizing the likelihood of a tear in the leaflets due to suturing.

Figure 4C:
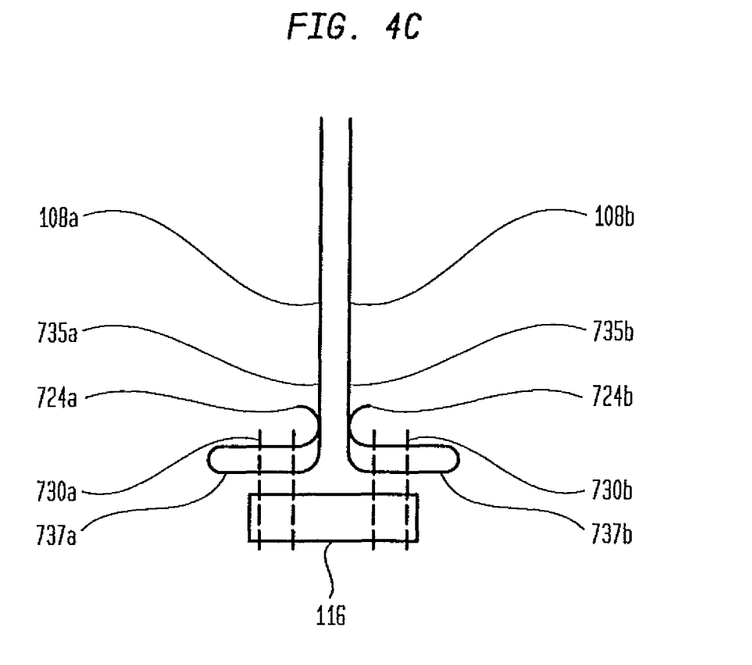

FIG. 4C illustrates a variant of the embodiment of FIG. 4B. In the embodiment of FIG. 4C, the end portions 722a, 722b have much larger unsutured free edges 724a, 724b, respectively, which extend toward the immediate adjacent portions 735a, 735b of the leaflets 108a, 108b, respectively, and then curl back toward the U-shaped pleats 737a, 737b, respectively. This configuration reduces the possibility of tearing the free edges 724a, 724b of end portions 722a, 722b due to the stress induced by the suturing.

Figure 4D:
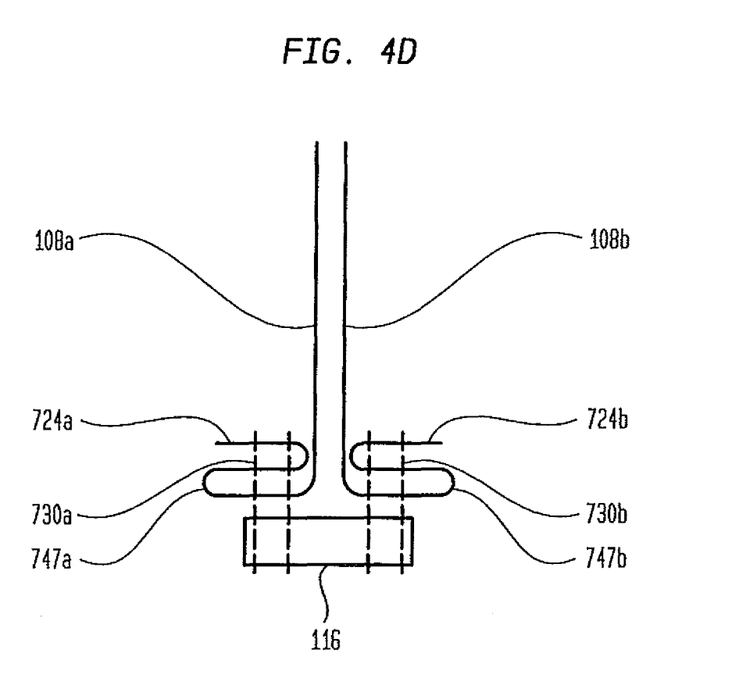

Referring to FIG. 4D, the embodiment illustrated is generally similar to the embodiments of FIGS. 4B and 4C. Whereas in the embodiments of FIGS. 4B and 4C, the end portions 722a, 722b of the leaflets 108a, 108b have a single fold in the form of U-shaped pleats 737a, 737b, respectively, the end portions 722a, 722b in the embodiment of FIG. 4D include multiple folds in a generally compressed "S-shaped" pleat or a Heintz pleat 747a, 747b, respectively. While two such folds are shown in FIG. 4D for the pleats 747a, 747b, it will be understood that pleats 747a, 747b may include more than two such folds. The additional folds in the embodiment of FIG. 4D further distribute the stresses due to suturing and reduce the likelihood of tearing the leaflets 108a and 108b.

Figure 4E:
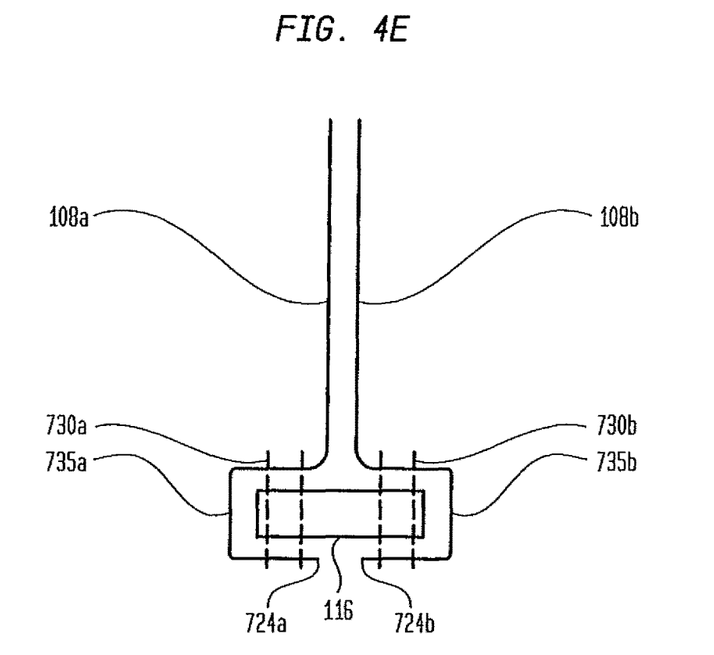

Now referring to FIG. 4E, leaflets 108a, 108b are sutured to the commissure point 116 according to another embodiment of the invention. The end portion 722a of leaflet 108a is wrapped around one side of commissure point 116 such that a U-shaped pleat 735a is formed, which generally envelopes one side of the commissure point. Likewise, the end portion 722b of leaflet 108b is wrapped around the other side of commissure point 116 such that a U-shaped pleat 735b is formed, which generally envelopes the other side of the commissure point. Thus, the commissure point 116 may be enveloped on opposing sides by the end portions 722a and 722b, respectively. One or more sutures 730a (one pair of suture illustrated) attach the end portion 722a to the commissure point 116, and one or more sutures 730b (one pair of suture illustrated) attach the end portion 722b to the commissure point 116. The suturing sites on the end portions 724a and 724b are situated further apart due to the presence of the commissure point 116, thereby reducing the stress due to suturing in the leaflets 108a and 108b. Note that this type of arrangement might necessitate some change in how and where the cuff 106 is attached. It could be attached on the ablumenal surface over the free ends 724a, 724b. In other configurations, the cuff 106 could also be split in the proximity of the commissure point 116 so that either end may be attached over the top of the inner portion of the folds.

The cuff 106 could also be attached to the lumenal surface but disposed between and under the commissure points and the proximal end of the stent. These types of cuff arrangements may also be used in connection with, for example, the embodiments illustrated in FIGS. 4F and 4G.

Figure 4F:
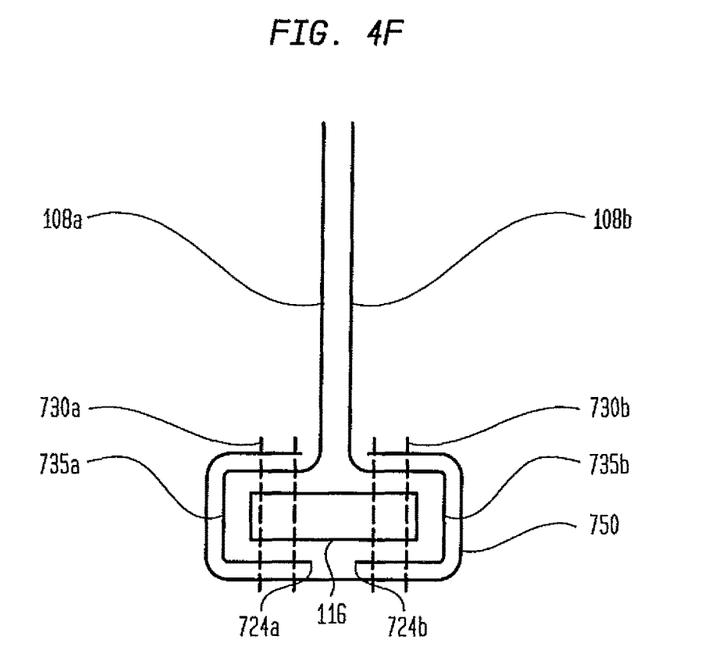

FIG. 4F illustrates an embodiment which generally includes the features of the embodiment illustrated in FIG. 4E. In particular, the end portion 722a of the leaflet 108a is wrapped around one side of commissure point 116 such that a U-shaped pleat 735a is formed which envelopes one side of the commissure point 116. The end portion 722b of the leaflet 108b is wrapped around the other side of the commissure point such that a U-shaped pleat 735b is formed which envelopes the other side of the commissure point 116. A tissue or fabric web 750 is then wrapped around the end portions 722a, 722b and the commissure point 116 from the outside surface (the bottom as seen in FIG. 4F) so as to cover any gap between the free ends 724a and 724b. One or more sutures 730a, 730b (one pair of sutures illustrated for each leaflet 108a, 108b) may attach the web 750 and the end portions 722a, 722b to the commissure point 116. In an exemplary configuration, the web 750 may be formed from any suitable biological material or polymer. Examples of biological materials suitable for the web 750 include, but are not limited to, porcine or bovine pericardial tissue. Examples of polymers suitable for the web 750 include, but are not limited to, polyurethane and polyester. The web 750 provides reinforcement to the end portions 722a, 722b and reduces the stress induced therein due to the suturing.

Figure 4G:
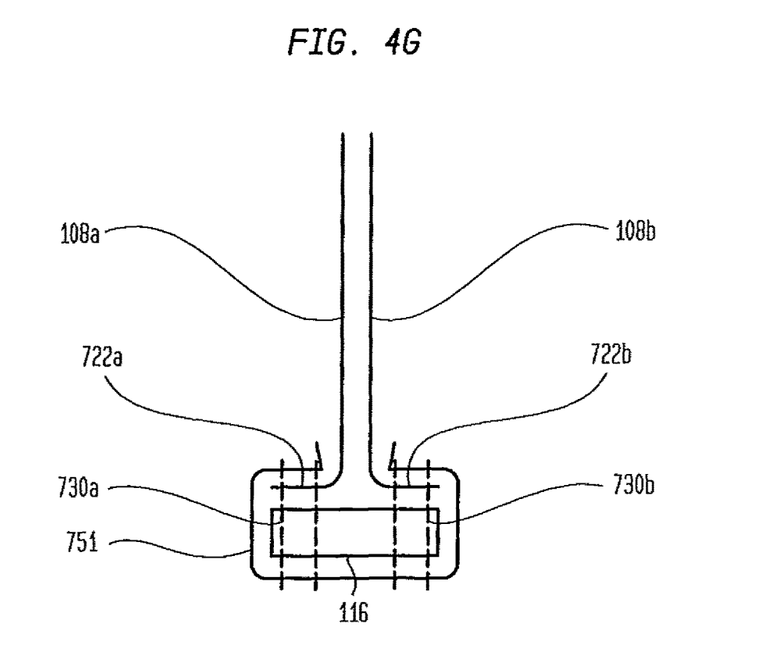

In yet another embodiment illustrated in FIG. 4G, which is a variation of the embodiment illustrated in FIG. 4F, the end portions 722a, 722b of the respective leaflets 108a, 108b generally overlie the commissure point 116 in an L-shaped fold, but do not wrap around the same. A fabric or tissue web 751 is then wrapped around the commissure point 116 so as to overlie the end portions 722a, 722b of the leaflets 108a, 108b. In an exemplary embodiment, the web 751 may be formed from the same materials as may be used for forming the web 750. One or more sutures 730a (one pair of sutures illustrated) may attach the web 751 and the end portion 722a to the commissure point 116. Likewise, one or more sutures 730b (one pair of sutures illustrated) may attach the web 751 and the end portion 722b to the commissure point 116. The web 751 provides reinforcement to the end portions 722a, 722b and reduces the stress induced therein due to the suturing.

Figure 4H:
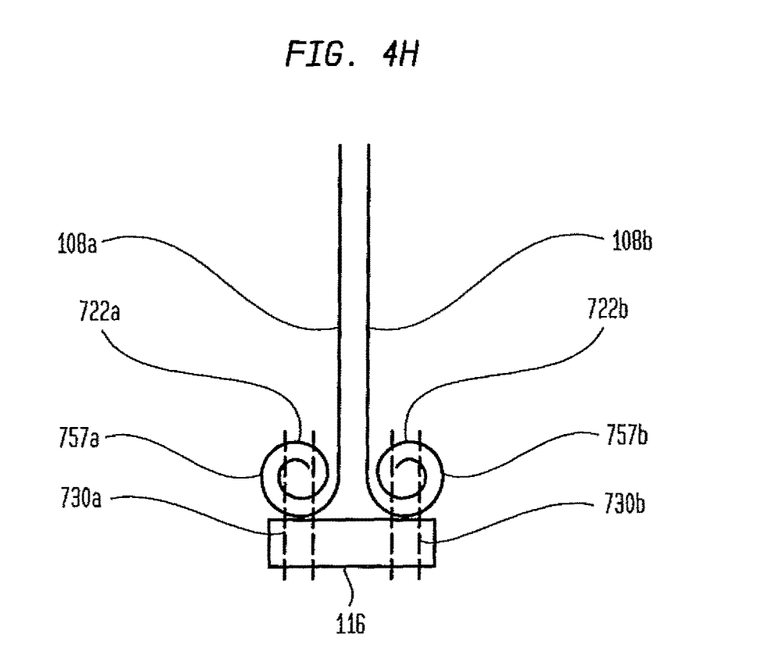

Referring now to FIG. 4H, leaflets 108a, 108b are sutured to the commissure point 116 according to yet another embodiment of the invention. The end portions 722a, 722b of the respective leaflets 108a, 108b are rolled into a generally spiral configuration 757a, 757b, respectively. The rolled end portions 722a, 722b may be sutured to the commissure point 116 via one or more sutures 730a, 730b, respectively. An advantage of the rolled end portions 722a, 722b is that the stresses caused by the sutures 730a, 730b are evenly distributed over the end portions 722a, 722b.

Figure 4I:
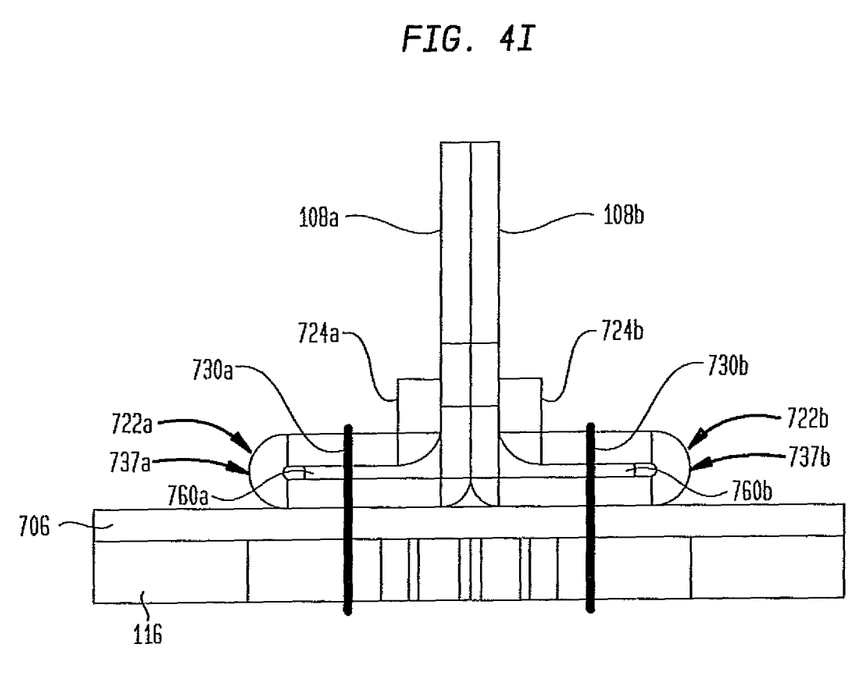

FIG. 4I illustrates another exemplary embodiment of the invention. Each of the end portions 722a, 722b of the respective leaflets 108a, 108b is folded into a generally "U-shaped" pleat 737a, 737b, respectively. A cuff 706 is interposed between the U-shaped pleats 737a, 737b and the commissure point 116. The free ends 724a, 724b of the respective end portions 722a, 722b are attached to respective remainder portions of the leaflets 108a, 108b. Reinforcement tissue or fabric webs 760a, 760b are disposed, respectively, between the folds of each of the end portions 722a, 722b. The webs 760a, 760b may be formed from the same biological or polymeric materials as may be used for forming the web 750. One or more sutures 730a attach the folded end portion 722a along with the web 760a and the cuff 706 to the commissure point 116, while one or more sutures 730b attach the folded end portion 722b along with the web 760b and the cuff 706 to the commissure point. The webs 760a, 760b reinforce the folded portions 722a, 722b.

Figure 5A:
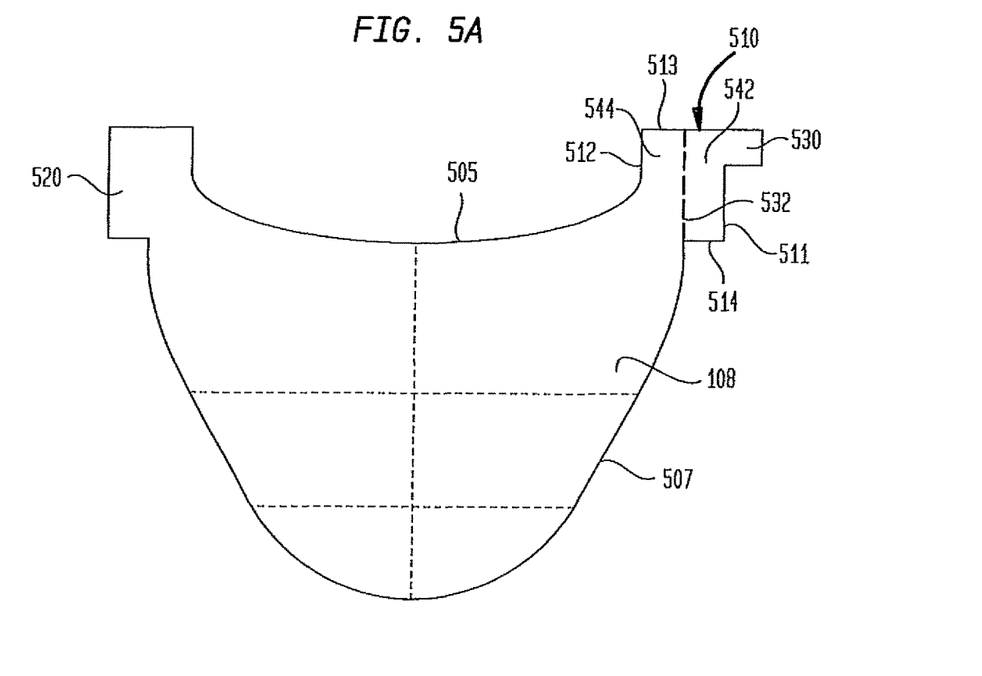
FIGS. 5A-5B are highly schematic front elevational views of two embodiments of the leaflets according to aspects of the present invention.

FIG. 5A schematically illustrates the leaflet 108, which may be sutured to the commissure point 116 of the stent 102 using any of the configurations described above. Leaflet 108 has a free edge 505 and an arcuate edge 507 attached, for example, to one or more struts 114 of the stent 102 as described above. Leaflet 108 may include a generally rectangular tab 510 at one end of the free edge 505 and another generally rectangular tab 520 at the other end of the free edge 505. The tab 510 may be defined by a substantially straight outside edge 511, a substantially straight inside edge 512, that is substantially parallel to the edge 511, a substantially straight top edge 513, and a substantially straight bottom edge 514, that is substantially parallel to the top edge 513 and substantially orthogonal to the edges 511 and 512. The tab 510 may include a further projection 530 projecting laterally from the outside edge 511. The tab 520 may be substantially the same the tab 510, but may omit the further projection 530.

As noted, the leaflet 108 may be attached to the commissure point 116 of the stent 102 using any of the configurations previously described. The following will describe the attachment of the leaflet 108 to the commissure point 116 using the configuration of FIG. 41. The tab 510 may include an imaginary fold line 532, which is generally aligned with the arcuate edge 507 of the leaflet 108, and is substantially parallel to the edges 511 and 512, dividing the tab 510 into a first portion 542 and a second portion 544. The tab 510 may be folded along the fold line 532 to form, for example, the generally "U-shaped" pleat 737a shown in FIG. 41.

Figure 5B:
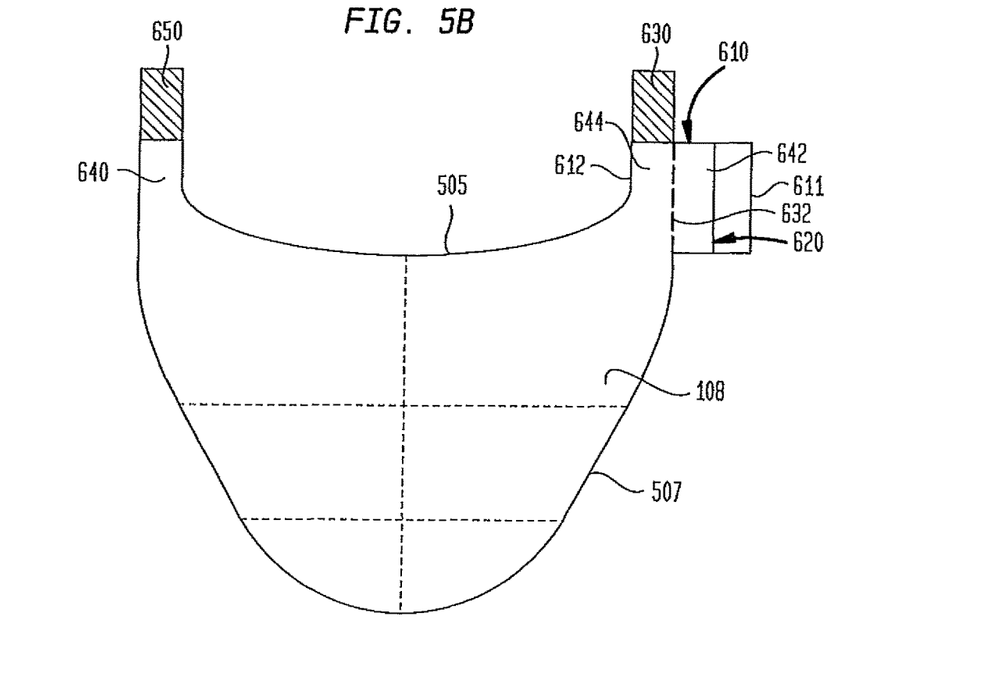
Figure 5C:
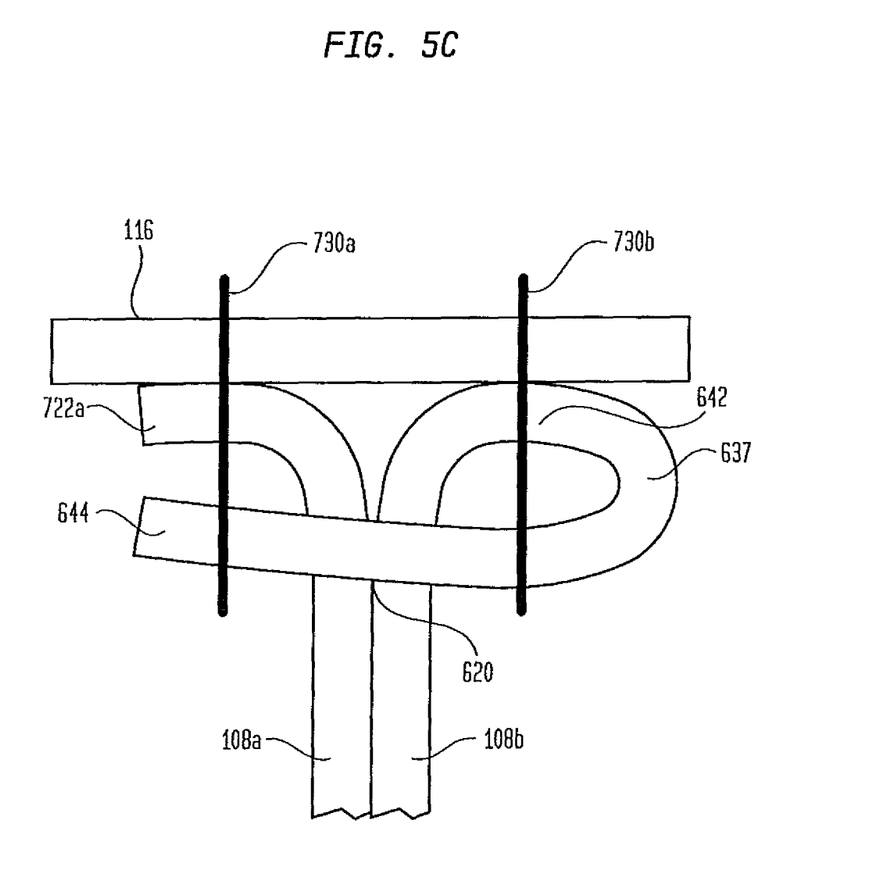
FIG. 5C is a highly schematic end view showing an embodiment of leaflet suturing to a commissure point according to an aspect of the present invention.

FIGS. 5B and 5C illustrate yet another embodiment of the leaflet 108 and the suturing of the leaflet to the commissure point 116. The leaflet 108 may be generally similar to the leaflet 108 of FIG. 5A, except for the differences set forth below. The leaflet 108 may include a generally rectangular tab 610, similar in configuration to the tab 510 of FIG. 5A, extending from one end of the free edge 505, and a similar generally rectangular tab 640 extending from the other end of the free edge 505. Rather than having a further projection extending from the outside edge as with tab 510, however the tab 610 may optionally have a further projection 630 extending from the top edge 613. A similar further projection 650 may extend from the top edge of the tab 640.

As noted, the leaflet 108 may be attached to the commissure point 116 of the stent 102 using any of the configurations previously described. Yet another configuration for attaching the leaflet 108 to the commissure point 116 is shown in FIG. 5C. The tab 610 may include an imaginary fold line 632, which is generally aligned with the arcuate edge 507 of the leaflet 108 and one edge of further projection 630, and is substantially parallel to the outside edge 611 and the inside edge 612 of tab 610, dividing the tab 610 into a first portion 642 and a second portion 644. A generally vertical slit 620, as seen in FIG. 5E, is defined in the first portion 642 of the tab 610 and is substantially parallel to the edges 611 and 612. The tab 610 may be folded along the fold line 632 to form a generally "U-shaped" pleat 637 which extends across leaflets 108a, 108b. The slit 620 accommodates portions of the free edges of the leaflets 108a, 108b. One or more sutures 730a attach the folded second portion 644 of the leaflet 108b and the free end 722a of the leaflet 108a to the commissure point 116. One or more sutures 730b attach the U-shaped pleat 637 to the commissure point 116. Where the tab 610 includes further projection 630, the further projection may be tacked to the stent and then later removed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
a collapsible and expandable stent having a proximal end and a distal end and comprising a plurality of struts and a plurality of cells defined by the plurality of struts;
a plurality of commissure points disposed on the stent, each of the commissure points including a body having an inner surface, an outer surface, a first lateral side and a second lateral side, each of the commissure points interconnecting first and second adjacent cells in an annular row of the stent such that the first lateral side faces the first cell and the second lateral side faces the second cell; and
a collapsible and expandable valve assembly disposed within the stent, the valve assembly including a plurality of leaflets, each leaflet having an end portion;
wherein the end portion of a first one of the leaflets includes a first folded portion and a first remainder portion, the first remainder portion having a first segment coextensive with the first folded portion and a second segment extending from the first segment away from one of the commissure points, the first folded portion of the first leaflet being attached to the one commissure point in contact with the inner surface of the one commissure point,
wherein the end portion of a second one of the leaflets adjacent the first leaflet includes a second folded portion and a second remainder portion, the second remainder portion having a first segment coextensive with the second folded portion and a second segment extending from the first segment of the second remainder portion away from the one commissure point, the second folded portion of the second leaflet being attached to the one commissure point in contact with the inner surface of the one commissure point,
wherein the first folded portion of the first leaflet is attached directly to the first segment of the first remainder portion of the first leaflet so that a surface of the first folded portion contacts a surface of the first segment of the first remainder portion, and
wherein the second folded portion of the second leaflet is attached directly to the first segment of the second remainder portion of the second leaflet so that a surface of the second folded portion contacts a surface of the first segment of the second remainder portion.

2. The prosthetic heart valve according to claim 1, wherein the first folded portion and the first segment of the first remainder of the first leaflet are generally parallel to the second segment of the first remainder of the first leaflet.

3. The prosthetic heart valve according to claim 1, wherein the first folded portion and the first segment of the first remainder of the first leaflet are generally perpendicular to the second segment of the first remainder of the first leaflet.

4. The prosthetic heart valve according to claim 3, wherein a free edge of the end portion of the first leaflet extends beyond a suture away from the first remainder portion of the first leaflet.

5. The prosthetic heart valve according to claim 3, wherein the end portion of the first leaflet is folded so that the first folded portion of the first leaflet includes at least two layers of the end portion of the first leaflet.

6. A prosthetic heart valve, comprising:
a collapsible and expandable stent having a proximal end and a distal end and comprising a plurality of struts and a plurality of cells defined by the plurality of struts;
a plurality of commissure points disposed on the stent, each of the commissure points including a body having an inner surface, an outer surface, a first lateral side and a second lateral side, each of the commissure points interconnecting first and second adjacent cells in an annular row of the stent such that the first lateral side faces the first cell and the second lateral side faces the second cell; and a collapsible and expandable valve assembly disposed within the stent, the valve assembly including a plurality of leaflets, each leaflet having an end portion;

wherein the end portion of a first one of the leaflets includes a first folded portion and a first remainder portion, the first remainder portion having a first segment coextensive with the first folded portion and a second segment extending from the first segment away from one of the commissure points, the first folded portion of the first leaflet being attached to the one commissure point in contact with the inner surface of the one commissure point, the first folded portion having a configuration selected from the group consisting of a U-shaped pleat, an S-shaped pleat, and an L-shaped fold;

wherein the end portion of a second one of the leaflets adjacent to the first leaflet includes a second folded portion and a second remainder portion, the second remainder portion having a first segment coextensive with the second folded portion and a second segment extending from the first segment away from the one commissure point, the second folded portion of the second leaflet being attached to the one commissure point in contact with the inner surface of the one commissure point, the second folded portion having a configuration selected from the group consisting of a U-shaped pleat, an S-shaped pleat, and an L-shaped fold;

wherein the first folded portion of the first leaflet is attached directly to the first segment of the first remainder portion of the first leaflet so that a surface of the first folded portion contacts a surface of the first segment of the first remainder portion; and wherein the second folded portion of the second leaflet is attached directly to the first segment of the second remainder portion of the second leaflet so that a surface of the second folded portion contacts a surface of the first segment of the second remainder portion.

7. A prosthetic heart valve comprising:

a collapsible and expandable stent having a proximal end and a distal end;

a plurality of commissure points disposed on the stent, each of the commissure points including a body having an inner surface, an outer surface, a first side surface extending between the inner surface and the outer surface on a first lateral side of the body and a second side surface extending between the inner surface and the outer surface on a second lateral side of the body, each of the commissure points interconnecting a first cell adjacent to the first lateral side of the body and a second cell adjacent to the second lateral side of the body such that the first side surface faces the first cell and the second side surface faces the second cell; and a collapsible and expandable valve assembly disposed within the stent, the valve assembly including a plurality of leaflets, each leaflet having an end portion;

wherein a first end portion of a first one of the leaflets is at least partially wrapped about the first side surface of one of the commissure points and a second end portion of a second one of the leaflets is at least partially wrapped about the second side surface of the one commissure point, such that the first end portion and the second end portion form first and second U-shaped pleats, respectively, enveloping the first side surface and second side surface of the one commissure point, respectively; and wherein the first end portion and the second end portion are attached to the one commissure point, free ends of the first end portion and second end portions being independent of one another and facing one another.

8. The prosthetic heart of claim 7 further comprising a web of material overlying the end portion of the first leaflet and the end portion of the second leaflet and enveloping the first side surface and second side surface of the one commissure point, the web of material being attached to the end portion of the first leaflet, the end portion of the second leaflets and to the outer surface of the one commissure point.

9. A prosthetic heart valve comprising:

a collapsible and expandable stent having a proximal end and a distal end and comprising a plurality of struts and a plurality of cells defined by the plurality of struts;

a plurality of commissure points disposed on the stent, each of the commissure points including a body having an inner surface, an outer surface, a first side surface extending between the inner surface and the outer surface on a first lateral side of the body and a second side surface extending between the inner surface and the outer surface on a second lateral side of the body, each of the commissure points interconnecting a first cell adjacent to the first lateral side of the body and a second cell adjacent to the second lateral side of the body such that the first side surface faces the first cell and the second side surface faces the second cell;

a collapsible and expandable valve assembly disposed within the stent, the valve assembly including a plurality of leaflets, each leaflet having an end portion;

wherein the end portion of a first one of the leaflets and the end portion of a second one of the leaflets overlie the inner surface of one of the commissure points in an L-shaped configuration so that the first and second leaflets are adjacent to one another and contact the inner surface of the one commissure point;

wherein the end portion of the first leaflet extends from the first leaflet in a first direction toward the first lateral side of the one commissure point and is attached to the one commissure point, a free end of the end portion of the first leaflet pointing in the first direction; and wherein the end portion of the second leaflet extends from the second leaflet in a second direction generally opposite the first direction toward the second lateral side of the one commissure point and away from the end portion of the first leaflet and is attached to the one commissure point, a free end of the end portion of the second leaflet pointing in the second direction; and a web wrapped around the one commissure point so as to overlie the end portion of the first leaflet, the end portion of the second leaflet, the first lateral side and the second lateral side and the outer surface of the one commissure point.

* * * * *